United States Patent [19]

Duthoit

[11] Patent Number: 5,395,384
[45] Date of Patent: Mar. 7, 1995

[54] INSTRUMENT FOR THE EXTRACTION OF PATHO-LOGICAL VEIN SECTIONS SUCH AS VARICES

[76] Inventor: Francois R. Duthoit, 8 rue du Débouché Neuf, 59320 Escobecques (Nord), France

[21] Appl. No.: 158,692

[22] Filed: Nov. 29, 1993

[30] Foreign Application Priority Data

Dec. 30, 1992 [FR] France .................. 92 16061

[51] Int. Cl.6 ............................................. A61B 17/00
[52] U.S. Cl. .................................................... 606/159
[58] Field of Search .................... 128/657, 772; 606/1, 606/106, 108, 159, 190

[56] References Cited

U.S. PATENT DOCUMENTS

| | | | |
|---|---|---|---|
| 2,661,003 | 12/1953 | Dexine et al. | 606/159 |
| 3,045,676 | 7/1962 | Slaten | 606/159 |
| 3,508,553 | 4/1970 | Kanbar et al. | 606/159 |
| 3,568,677 | 3/1971 | Nolan | 606/159 |
| 3,788,325 | 1/1974 | Jacobsen | 606/159 |
| 4,528,982 | 7/1985 | Wellenstam | 606/159 |
| 5,011,489 | 4/1991 | Salem | 606/159 |

FOREIGN PATENT DOCUMENTS

| | | | |
|---|---|---|---|
| 2062204 | 8/1971 | Germany | 606/159 |
| 3427128 | 1/1986 | Germany | 606/1 |
| 3717926 | 12/1988 | Germany | 606/159 |
| 1597180 | 10/1990 | U.S.S.R. | 606/1 |

*Primary Examiner*—Stephen C. Pellegrino
*Assistant Examiner*—Glenn Dawson
*Attorney, Agent, or Firm*—Harrison & Egbert

[57] ABSTRACT

Instrument (1) designed, in particular, to permit the extraction of vein sections such as, for example, varices, including a two-piece supple cable (2) that is flexible and strong, both ends of which support a bullet shaped member (3).

The cable (2) has a diameter substantially smaller than that of the vein to be extracted, and a length corresponding substantially to at least the length of the vein. The two cables are connected end to end by complementary connecting pieces. An olive-shaped member holds the connecting pieces within an internal bore. The bullet shaped members have a radial orifice for receiving a thread to assist in endo-stripping of the vein section.

11 Claims, 5 Drawing Sheets

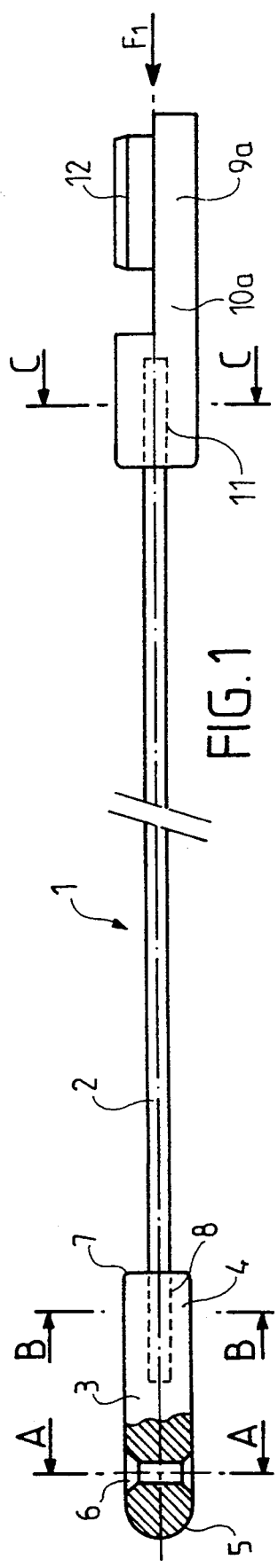
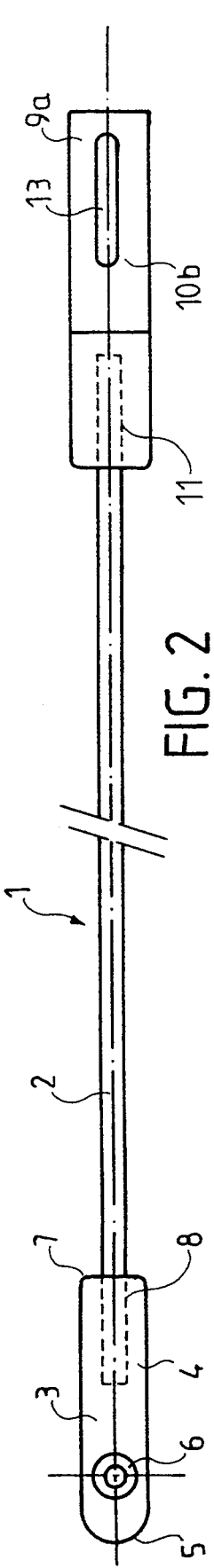
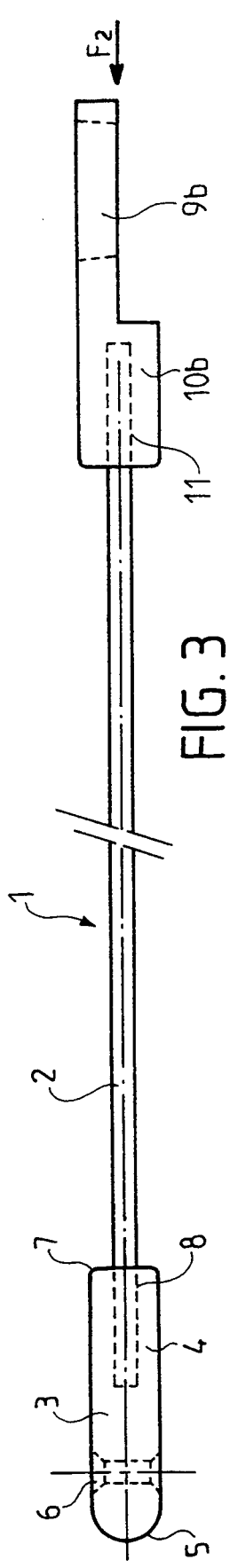
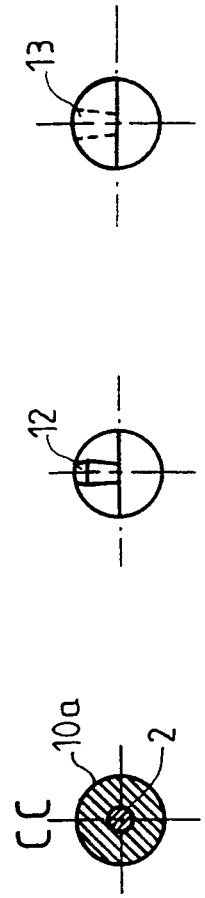
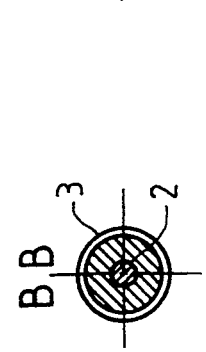
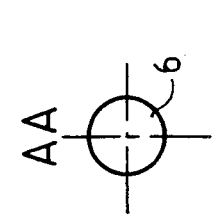

E-E

F-F

INSTRUMENT FOR THE EXTRACTION OF PATHO-LOGICAL VEIN SECTIONS SUCH AS VARICES

TECHNICAL FIELD

The present invention relates to an instrument designed, in particular, to permit the extraction of pathological vein sections such as varices.

It will find an application, in particular, in the field of manufacture of such instruments, as well as in the field of surgery.

At the present time, various techniques are used to

BACKGROUND ART

At the present time, various techniques are used to extract varices in a varicose blood transporting vein, for example the long saphenous vein.

The treatment of varices further makes use of various techniques, including "stripping". This technique is used when a vein segment is pathological and irretrievably damaged. When this segment is short, stripping can be carried out with visual monitoring, after the vein segment to be removed has been completely exposed.

When the segment is long, stripping has to be carried out in a different way using a "semi-blind" technique, which involves stripping the majority of the vein segment without visual monitoring, the latter being possible only in the area of its proximal and distal ends, by means of a short incision allowing the vein to be identified, dissected and catheterized, either downwards or upwards, using instruments.

For this purpose, there is known, in particular, the so-called "exo-stripping" technique, which consists in extracting a section of vein by stripping it away with the use of an instrument that comprises a flexible wire one of the ends of which has a cone shape and the other end of which has an olive shaped member.

Using such an instrument, the surgeon, when removing varices from a leg, bares the vein below the location of the hernia and introduces the bullet shaped end so as to cause the said end substantially to pass the area of the hernia to be extracted. When this introduction operation is carried out, the vein is engaged by the olive shaped member, the diameter of which is far greater than that of the vein. The vein section is then removed by the surgeon, who pulls on the instrument, causing it to emerge in the area of second incision made in the patient's leg.

Such techniques have many drawbacks, in practice, in particular that of necessitating two incisions, on one hand, when the instrument is introduced and, on the other hand, when it is removed.

Furthermore, such instruments are not always suitable for enabling relatively long sections of vein to be extracted, as this may necessitate a large number of incisions, which can be prejudicial to the patient.

It should also be noted that the use of such surgical instruments can give rise to traumatisms of the saphenous vein which result, furthermore, from the surgeon's pulling on the vein and/or the large number of incisions required for such operations.

There is also known the so-called "internal stripping" technique, which consists in removing the vein from the leg by stripping it off using a cable that has been previously inserted inside it. In addition, using this technique, the surgeon extracts a section of vein from the living tissue through which it passes it by causing it to slide gradually against the said tissue, and by exerting an action so that the end of the said section folds longitudinally.

In this technique, the vein is folded back on itself in order to reduce peri-veinous traumatism. The olive shaped member used in "exo-stripping" and having a diameter greater than that of the vein is replaced, here, either by a simple wire joining the cable, to which it is tied during the operation, on the end of the vein to be folded back on itself, or by an intermediate device connecting two cables by means of their respective ends adapted to be interconnected, in particular by snap fastening, and thus to permit stripping, in an alternating movement, of the vein, which has been previously joined to the cable by a strong ligature, pressing in front of or behind this connection according to the direction of traction.

Thus, the instruments used in phlebectomy by catheterism presently known include a long, flexible body such as a cable, for example, the terminal portions of which have a bulge or excrescence further permitting the installation of a pulling handle and/or a means of blocking the vein to be extracted.

These blocking means are, moreover, generally constituted by an element having a diameter at least equal to diameter of the terminal portion of the vein section to be extracted, and complementary shapes and means permitting its stowage and its installation on the excrescences of the said cable.

Now, in practice, such blocking means have numerous drawbacks and, in particular, they are not always easy to use. Furthermore, owing to their diameter, which is at least equal to the outside diameter of the conduit, the tissues are observed to be scraped during removal of the vein to be extracted, which gives rise to injuries and/or physiological traumatisms of the tissues which can be prejudicial to the patient.

Furthermore, the different nerves that are located adjacent to the saphenous vein are liable to be injured when such instruments are used, which makes such operations painful for the patient.

In addition, in practice, although more convenient to use, such devices do not give complete satisfaction as they do not always allow the vein section to be extracted to be held efficiently.

The object of the present invention is to remedy the drawbacks of the instruments designed, in particular, to permit the extraction of vein sections by providing an instrument that can be used to implement -endo and/or exo vein stripping techniques without risk to the patient.

Another object achieved by the instrument according to the invention resides in the fact that it is of simple, robust design, which increases its potential applications.

Another advantage of the instrument according to the invention resides in the fact that it is produced from materials having appropriate characteristics in conformity with the standards in force for such uses, in particular in the field of surgery.

Other objects and advantages of the present invention will emerge in the course of the following description, which is provided, however, only by way of illustration, and is not intended to limit same.

SUMMARY OF THE INVENTION

For this purpose, the invention provides an instrument, designed, in particular, to permit the extraction of vein sections such as, in particular, varices, including at least a cable that is flexible, supple and strong having a diameter that is substantially smaller than that of the vein to be extracted and one of the ends of which carries a bullet shaped member. It is characterized by the fact that the cable is of a short length corresponding substantially to at least the length of the vein to be extracted, and in that the bullet shaped member has a body in which is provided a radial perforation.

BRIEF DESCRIPTION OF THE DRAWINGS

The present invention will be clearly understood from reading the following description accompanied by the annexed drawings, wherein:

FIG. 1 is a front view illustrating a cable which supports a connecting piece for the instrument according to the invention;

FIG. 2 is a top view schematically illustrating a cable which supports a connection piece for the instrument similar to that in FIG. 1;

FIG. 3 is a front view schematically representing a cable which supports a connecting piece complementary to that illustrated in FIGS. 1 and 2, according to the invention;

FIG. 4 is a view along line A—A of FIG. 1;

FIG. 5 is a cross-sectional view along line B—B of FIG. 1;

FIG. 6 is a cross-sectional view along line C—C of FIG. 1;

FIG. 7 is a view in the direction of arrow $F_1$ in FIG. 1;

FIG. 8 is a view in the direction of arrow $F_2$ in FIG. 3;

DETAILED DESCRIPTION OF THE INVENTION

Figure 9:
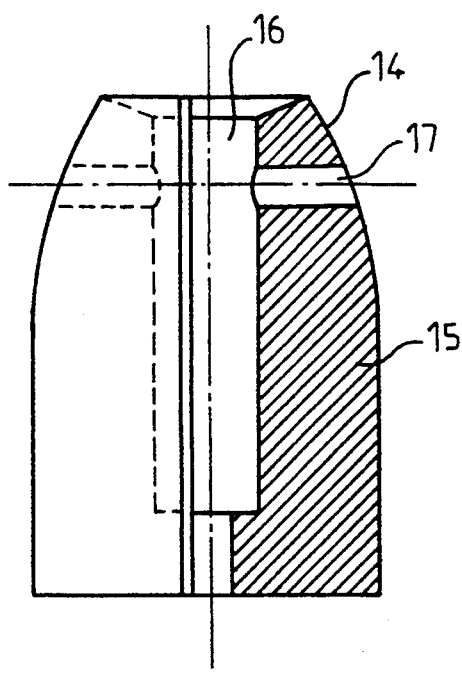
FIG. 9 is a partial cross-sectional schematic view of an olive shaped member of an instrument according to the invention.

The object of the present invention is an instrument designed, in particular, to permit the extraction of vein sections such as, for example, varices. It will find an application in the field of manufacture and use of such instruments of a medical and/or surgical type.

With more particular reference to FIGS. 1, 2 and 3, it can be seen that the instrument 1 according to the invention includes at least a flexible cable 2 which is supple and strong, and which is made, for example, from a plastic material or a metallic material having properties and characteristics compatible with standards for use, in particular on hygiene, in a hospital and/or medical environment.

In particular, good results have been obtained with a cable 2 made of polyester or "PET", or of polyamide.

This cable 2 further has a diameter compatible with that of the vein sections to be extracted and, in particular, an outside diameter slightly smaller than the inside diameter of the said vein sections.

The length of this cable 2 varies according to the application concerned and it can be, for example, between 1 m and 1.20 m long.

A bullet shaped member 3 is provided on the cable. In one form of embodiment, it has a body 4 of a generally cylindrical shape, rounded at its end 5 which is opposite to that of its connection to cable 2. It is further made of a plastic material or a metallic material having properties and characteristics appropriate for medical use.

The body 4 of the bullet shaped member also has, substantially opposite rounded end 5, a radial orifice 6 which passes right through it, as more especially illustrated in FIG. 4.

End 7 of body 4 of bullet shaped member 3, opposite rounded end 5, comprises an axial bore 8 extending substantially over at least one portion of the length of the said body 4 in order to enable one of the ends of cable 2 to be introduced and held therein in order to allow bullet shaped member 3 to be fastened thereon.

Figure 19:
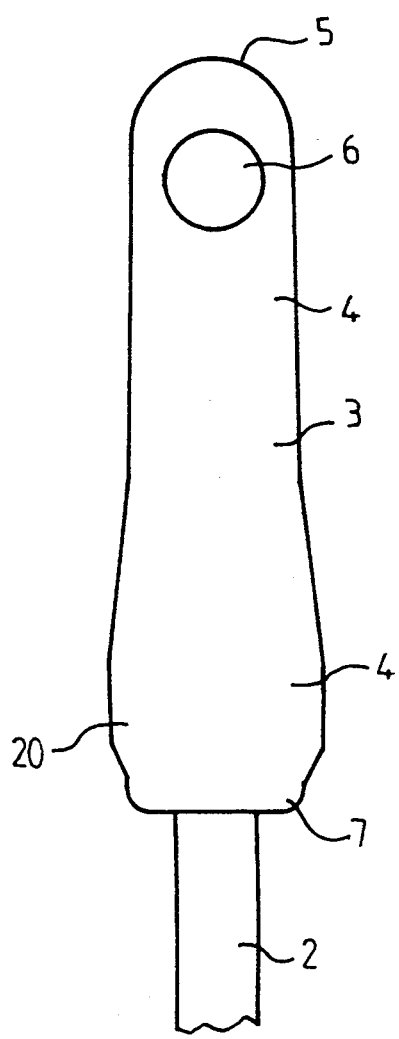
FIG. 19 is a schematic view showing an alterative form of embodiment of a bullet shaped member according to the invention.

In an alternative form of embodiment illustrated in FIG. 19, body 4 of bullet shaped member 3 has, on its end 7, a radial shoulder 20 the thickness and inclination of which are suitably chosen. This shoulder 20 makes it possible to facilitate the use of the device according to the invention in the case of sinuous veins or when passing through valvules, by enabling them, in particular, to be passed through more efficiently.

This cone member 3 is constituted by a body 4 having a diameter of 3.5 mm, for example, so as to permit catheterism of the saphenous vein when it is introduced into the said vein in order to permit extraction of the vein section that it is wished to remove.

Furthermore, the radial orifice 6 enables the vein to be fastened and held to ensure that it can be removed in accordance with the, endo-stripping technique, allowing it to be held and fastened via a thread, for example of polyester, on a return wire not represented, on which the surgeon pulls in order to remove the said vein section that it is wished to extract in the axis of the cable.

It should also be noted that, despite the flexibility of the vein to be extracted, this vein can rupture as a result of the tensile stresses set up by the detaching of its wall in the area of a collateral vein. In this case, it is then possible, according to the invention, to strip the said vein section by reversing the direction of traction and, in particular, by resuming the extraction operations from its sound end, that is to say by ligaturing the latter using the polyester thread in orifice 6.

Thus, the potential applications of the instrument are increased without the surgeon having to undertake lengthy, complex operations liable to generate secondary effects in the patient's body.

Figure 12:
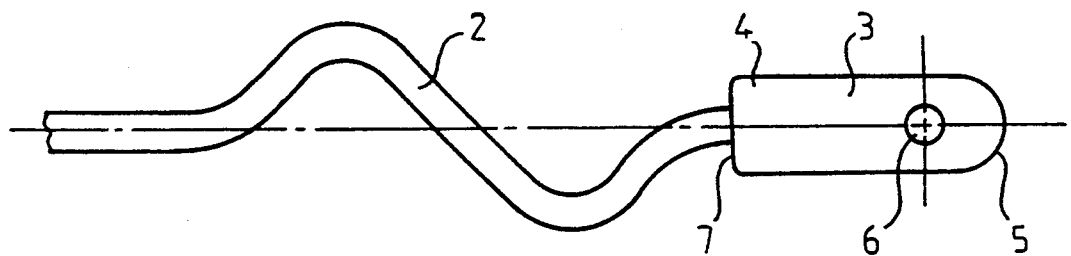
FIG. 12 is a schematic view illustrating a bullet shaped member of an instrument according to the inventions arranged at the end of a cable with a helical shape of a given pitch.
Figure 13:
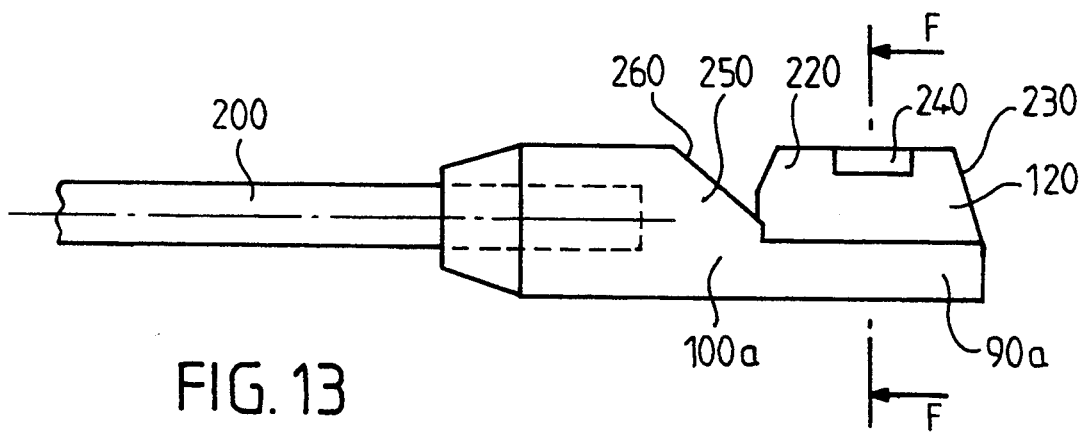
FIG. 13 is a schematic front view illustrating a cable supporting an alternative form of embodiment of a connection piece for the instrument according to the invention.
Figure 14:
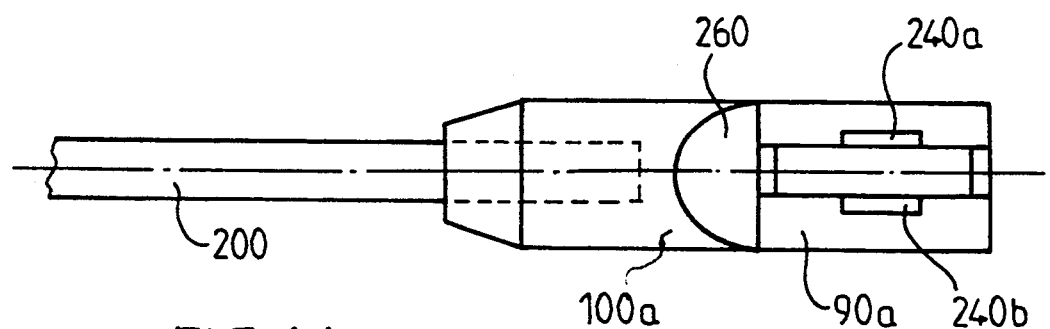
FIG. 14 is a top view schematically illustrating a cable which supports a connecting piece like that in FIG. 13.
Figure 15:
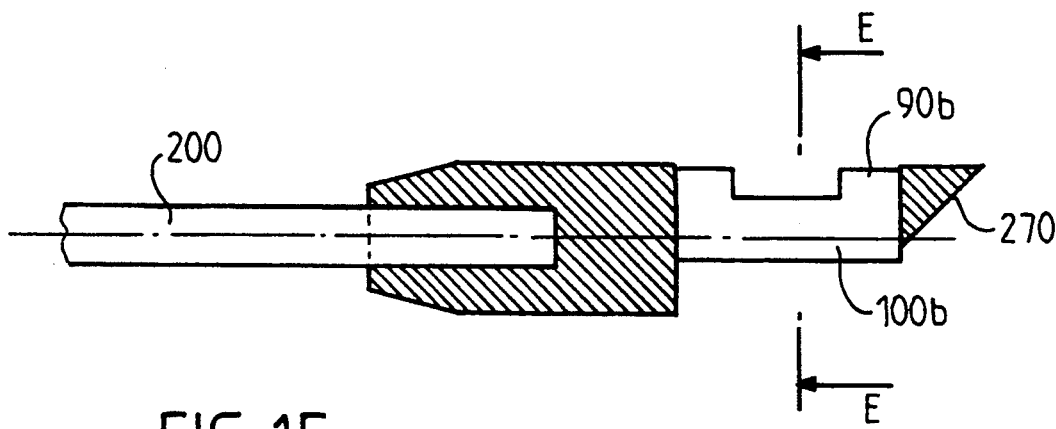
FIG. 15 is a cross-sectional schematic front view illustrating a cable which supports an alternative form of embodiment of a connecting piece complementary to those illustrated in FIGS. 13 et 14.
Figure 16:
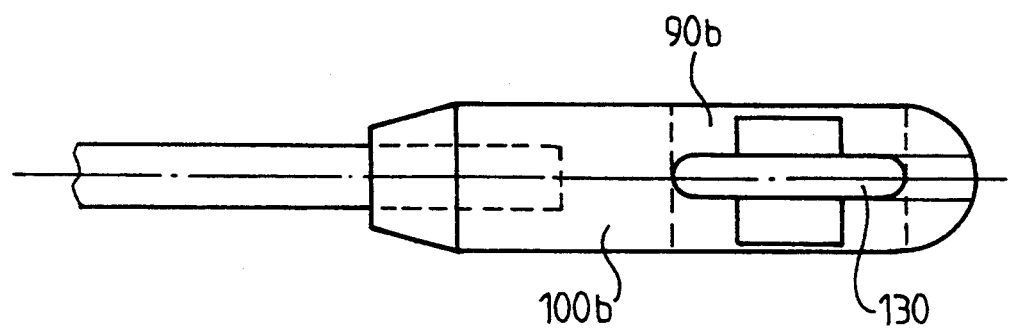
FIG. 16 is a top view which illustrates a piece similar to that of FIG. 16.
Figure 17:
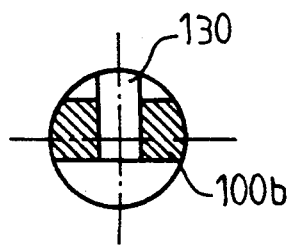
FIG. 17 is a cross-section along line E—E of FIG. 14.
Figure 18:
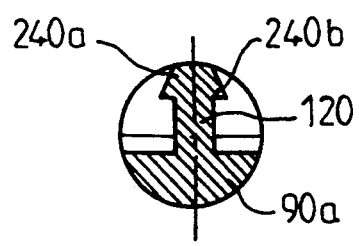
FIG. 18 is a cross-section along line F—F in FIG. 15.

Furthermore, in one particular form of embodiment of the invention, as more especially illustrated in FIG. 12, cable 2 has, in the vicinity of the end 7 of body 4 of bullet shaped member 3, a helical shape of a given pitch so as to permit and facilitate its introduction and placing inside the vein section to be extracted.

Of course, depending upon the applications and, in particular, the inside diameter of the vein to be extracted, the pitch of this section of helical cable will vary, as will the number of turns and/or undulations that it comprises.

The instrument 1 according to the invention also comprises complementary connecting pieces, male and female respectively, 9a-9b, made of a plastic material or of a metallic material, which has properties and characteristics that permit its use in medical and/or surgical applications.

These complementary connecting pieces 9a-9b respectively have a body 10a-10b in which is provided an axial orifice 11 fixed substantially on a portion of its length, and inside which is placed one of the ends of cable 2 in such a way as to permit the holding and securing of these connecting pieces on the said cable 2.

Figure 21:
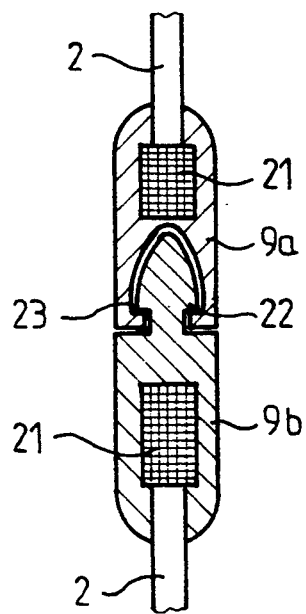
FIG. 21 is a cross-sectional schematic view illustrating the structure of the end of the cable inserted into the connecting piece.

As regards the holding of cable 2, in these connecting pieces 9a-9b, their ends 21 are crushed, as more especially represented in FIG. 21 in order to impart thereto a grid pattern produced by longitudinal and transverse striations substantially perpendicular to one another.

In one form of embodiment illustrated in FIGS. 1 and 2, body 10a of connecting piece 9a comprises a perpendicularly projecting stud 12 which is designed to cooperate, in mounted position, as will be described subsequently, with an orifice 13 having a shape matching that of stud 12 provided in body 10b of the complementary connecting piece 9b secured to the end of a cable 2, illustrated in FIG. 3.

Thus, according to the invention, it is possible to produce, on the basis of instrument 1, an association of a cable 2 such as the one illustrated in FIGS. 1 and 2 with, a cable such as the one illustrated in FIG. 3. This association is obtained through the the cooperation of stud 12 of body 10a of connecting piece 9a, which comes into position inside orifice 13 provided in body 10b of complementary connecting piece 9b.

Because of this association of two cables, it is possible to produce a connection that enables the surgeon to extract a vein segment using the endo-stripping technique without this necessitating the use of a return wire, which facilitates his work, while limiting the risks run by the patient.

Furthermore, in the event of it being impossible to implement the endo-stripping, through the connection of two cables, instrument 1 according to the invention also makes it possible to implement the exo-stripping technique, in the same direction of traction as that is implemented in the case of the endo-stripping technique, which increases its potential applications while enabling the practitioner to conduct the vein extraction operation under good conditions.

The benefit of using the instrument 1 according to the invention for implementing the exo-stripping technique are appreciable, particularly in the event of a rupture occurring, through the endo-stripping technique, in the area of a collateral vein. It is possible, with the present invention, to retrieve the olive shaped member by means of a return wire, through the incision via which it has been introduced.

In an alternative form of embodiment, there is provided a connecting piece the body 100a of which comprises a stud 120 having cants 220–230, as well as two longitudinal ribs 240a–240b extending on either side of the body, projecting substantially in its median portion. In addition, the end 250 of body 100a of connecting piece 90a also has a cant 260, at an appropiate angle of inclination, for example 58°.

Body 100b of connecting piece 90b comprises an oblong orifice 130 the shape of which matches that of stud 120 and which is designed to receive it in order to ensure the association of the two cables. Furthermore, body 100b of connecting piece 90b has cants 270 at an angle of inclination matching that of cant 260.

In this form of embodiment, the two cables are associated by the snap fastening of stud 120 into orifice 130, and this operation is facilitated, in particular, via ribs 240a–240b, which also, moreover, enable the matching pieces, male and female respectively, 90a–90b to be held relative to one another. Furthermore, these cants 260–270 also facilitate the removal of the stud from the orifice when it is desired to dissociate the two cables 200.

Figure 22:
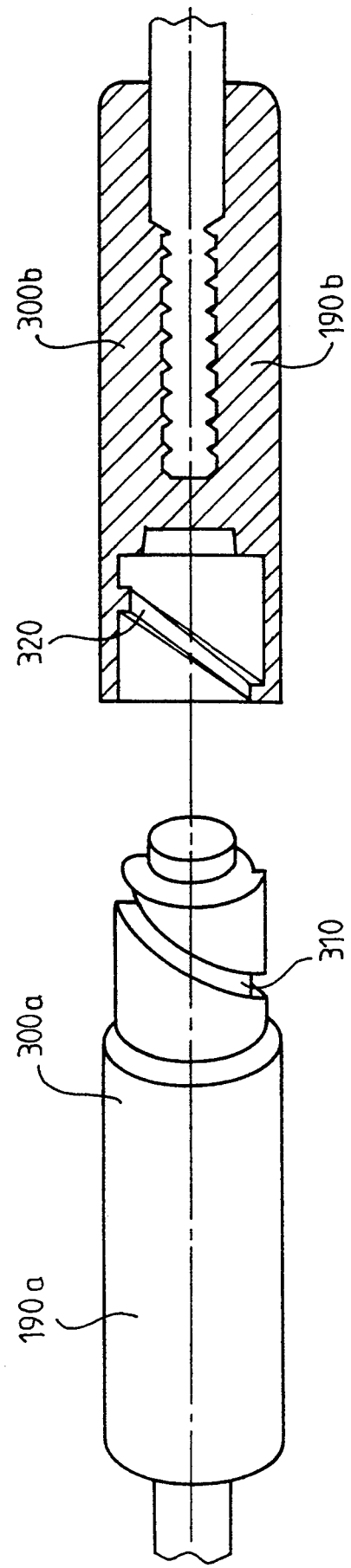
FIG. 22 is a schematic view in partial cross-section illustrating an alternative form of embodiment of the coupling means for the two complementary pieces.

In an alternative form of embodiment illustrated in FIG. 22, the body 300a of piece 190a, at one of its ends, has a threaded portion 310 of a given pitch. In this case, body 300b of complementary connecting piece 190b comprises, at one of its ends, a tapped portion 320 having a given pitch matching that of threaded portion 310 so as to enable these two pieces, 190a–190b, to be rendered integral with one another when the two cables are assembled.

One could, of course, also contemplate joining the two complementary pieces using any appropriate means that ensures suitable retention and holding compatible with the use of the device.

Thus, as illustrated in FIG. 21, body 10b of piece 9b comprises an end piece 22 having an appropriate shape according to the applications concerned, such as, for example, that of a rounded truncated cone suitable for cooperating by snap fastening with an orifice 23 of matching shape provided in body 10a of piece 9a.

Figure 10:
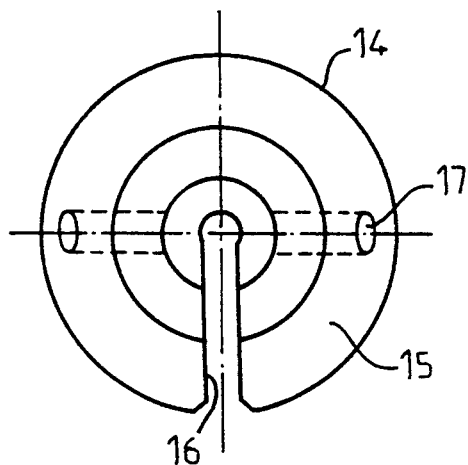
FIG. 10 is a top view of the olive shaped member of the instrument according to the invention.
Figure 11:
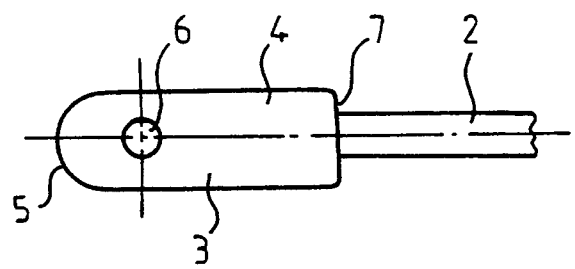
FIG. 11 is a schematic view illustrating a bullet shaped member of an instrument according to the invention.

Instrument 1 of the invention also comprises an olive shaped member 14, as illustrated in FIGS. 9 and 10, which is substantially frustoconical in shape and which is made of a plastic material or a metallic material suitable for such medical applications. This olive shaped member 14 has a body 15 inside which is provided a bore 16 permitting its cooperation with, and installation on, the connecting pieces 9a–9b. Bore 16 of olive-shaped member 14 slidably receives the connecting pieces 9a–9b therein. The cable 2 attached to the connecting pieces 9a–9b extends outwardly of bore 16.

It should also be noted that body 15 of olive shaped member 14 is removably installed on the connecting pieces 9a–9b simply and swiftly. This facilitates its fitting and removal so as to enhance the benefits of hence the use of instrument 1.

Furthermore, body 15 of cone member 14 also comprises a radial orifice 17 in order to enable a return wire to be fixed therein so that, in particular, the vein to be extracted can be removed separately from the dispositive, which further makes it possible to avoid traumatisms in the area of the saphenous nerve, thus making for a smaller scar.

Figure 20:
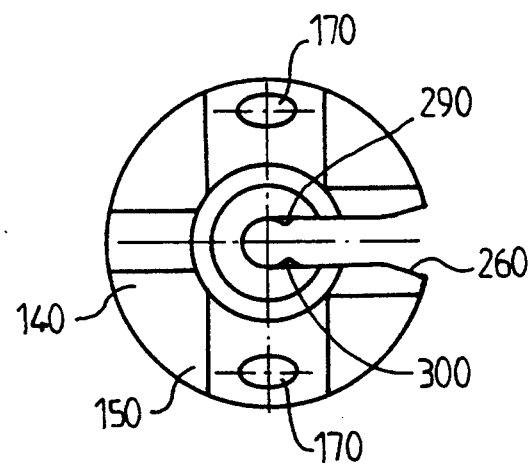
FIG. 20 is a top view illustrating an alternative form of embodiment of a bullet shaped member according to a "parrot's beak" configuration.

In a form of embodiment illustrated in FIG. 20, body 150 of olive-shape member 140 has an axial slot 160 to permit the installation and holding of the connectors and a fraction of cable length. More precisely, this housing, termed a "parrot's beak" comprises two parallel projecting ridges 290 and 300 disposed opposite one another to ensure that the cable is held more efficiently inside it. A stop, not shown, is also provided on one of the ends of the housing to retain the connectors when the latter is placed inside it, as well as a radial housing for fixing therein a return wire.

Other implementations of the present invention could, of course, have been contemplated without thereby departing from the scope thereof.

I claim:

1. An instrument for extraction of a vein section comprising:
   a first flexible cable having at one end a bullet-shaped member and at an opposite end a connecting piece, said bullet-shaped member having a radial orifice extending therethrough;
   a second flexible cable having a complementary connecting piece at one end and a bullet-shaped member at the other end, said complementary connecting piece detachably connected to said connecting piece of said first cable, said first and second cables having a diameter substantially less than a diameter of the vein section, said first and second cables having a length at least as long as the vein section; and
   an olive-shaped member of a substantially frustoconical shape, said olive-shaped member having an interior bore detachably receiving to the connecting pieces of said first and second cables.

2. The instrument according to claim 1, the connecting piece of one of said first and second cables comprises a body having a perpendicularly projecting stud.

3. The instrument according to claim 2, the complementary connecting piece comprises a body having an axial orifice of a shape that matingly receives the stud.

4. The instrument according to claim 1, said olive-shaped member having a radial orifice extending therethrough.

5. The instrument according to claim 1, the end of the first cable adjacent the bullet-shaped member has a helical shape of a given pitch.

6. The instrument according to claim 1, one of the bullet-shaped member has a substantially cylindrical body, one end of said bullet-shaped member being rounded.

7. The instrument according to claim 1, wherein one of the connecting pieces has a stud extending outwardly therefrom, said stud having cants formed on edges thereof, said stud having two longitudinal ribs extending substantially in a median portion of said stud.

8. The instrument according to claim 7, wherein the other of said connecting pieces has an oblong orifice having a shape that matches a shape of said stud, one of said connecting pieces having a canted surface that matches a canted surface on the other of said connecting pieces.

9. The instrument according to claim 1, wherein said interior bore of said olive-shaped member extends axially therethrough, said interior bore having two parallel projecting ridges disposed opposite one another to ensure the holding of the connecting pieces within the bore of said olive-shaped member.

10. The instrument according to claim 1, wherein one of the connecting pieces has a threaded portion formed thereon, said threaded portion received within a tapped portion in the other of the connecting pieces.

11. The instrument according to claim 1, wherein the first cable has a crushed portion at one end, said crushed portion having a grid pattern of longitudinal and transverse striations substantially perpendicular to one another.

* * * * *